United States Patent
Assmann et al.

(10) Patent No.: US 7,328,056 B2
(45) Date of Patent: Feb. 5, 2008

(54) MAGNETIC RESONANCE METHOD AND APPARATUS FOR CLASSIFYING AN ATHEROMA

(75) Inventors: Stefan Assmann, Erlangen (DE); Oliver Schreck, Bamberg (DE); Paul Finn, Chicago, IL (US); Stephanie Shors, Chicago, IL (US)

(73) Assignees: Siemens Aktiengesellschaft, Munich (DE); Northwestern University, Evanston, IL (US)

( * ) Notice: Subject to any disclaimer, the term of this patent is extended or adjusted under 35 U.S.C. 154(b) by 711 days.

(21) Appl. No.: 10/625,392

(22) Filed: Jul. 23, 2003

(65) Prior Publication Data

US 2005/0033178 A1 Feb. 10, 2005

(51) Int. Cl.
*A61B 5/05* (2006.01)

(52) U.S. Cl. ............... 600/420; 600/410; 600/419; 600/481; 382/128

(58) Field of Classification Search ............... 600/420, 600/19, 481, 410; 324/307; 382/128, 131, 382/132
See application file for complete search history.

(56) References Cited

U.S. PATENT DOCUMENTS 5,579,767 A * 12/1996 Prince .................. 600/420
6,415,048 B1 * 7/2002 Schneider ............. 382/131

OTHER PUBLICATIONS

Cai et al. Circulation. Classification of Human Carotid Atherosclerotic Lesions with In Vivo Multicontrast Magnetic Resonance Imaging. 106:1368-1373. Aug. 19, 2002.☐☐.*
Clarke et al. Identification of atherosclerotic plaque components using cluster analysis of multispectral MR images: comparison with histology. Proc. SPIE Int. Soc. Opt. Eng. 3978, 304-311. Apr. 2000.*
Choudhury et al. MRI and Characterization of Atherosclerotic Plaque: Emerging Applications and Molecular Imaging. Arterioscler. Thromb. Vasc. Biol. 2002. 22:1065-1074. Apr. 25, 2002.*
Mofidi et al. Angiogenesis in carotid atherosclerosis: the association with morphological features of plaque instability. British Journal of Surgery. 88:603. 2001.*
Flacke et al. Novel MRI Contrast Agent for Molecular Imaging of Fibrin: Implications for Detecting Vulnerable Plaques. Circulation. Sep. 11, 2001; 104(11):pp. 1280-1285.*

* cited by examiner

*Primary Examiner*—Brian L. Casler
*Assistant Examiner*—Parikha S. Mehta
(74) *Attorney, Agent, or Firm*—Schiff Hardin LLP (57) ABSTRACT

In a method and apparatus for classifying plaque in a blood vessel of a living subject using magnetic resonance imaging, a first magnetic resonance image is produced with a first intensity distribution of a cross-section of a vessel containing plaque, and a contrast agent is injected into the vascular system and a second magnetic resonance image of the cross-section of the vessel is produced with a second intensity distribution after a first time duration following the contrast agent injection, and a third magnetic resonance image of the cross-section of the vessel is produced with a third intensity distribution after a second time duration following the injection of the contrast agent, and the plaque is classified dependent on the respective intensity distributions of the magnetic resonance images.

33 Claims, 6 Drawing Sheets

MAGNETIC RESONANCE METHOD AND APPARATUS FOR CLASSIFYING AN ATHEROMA

BACKGROUND OF THE INVENTION

1. Field of the Invention

The present invention is directed to a method and apparatus for classifying an atheroma, and in particular to such a method and apparatus on the basis of magnetic resonance imaging.

2. Description of the Prior Art

Arteriosclerosis is a general term meaning a decrease in the natural elasticity of the wall of an artery. Such a decrease in elasticity can occur as a result of various pathological sources, one of which is the build-up of an atheroma, commonly referred to as a deposit or plaque, on or within the interior surface of the artery wall. Arteriosclerosis due to the presence of an atheroma is referred to atherosclerosis.

In addition to producing a health risk due to reduced cardiovascular efficiency, blockage or partial blockage of an artery, or any blood vessel, has the potential to cause the occurrence of a stroke. A stroke occurs when any of the significant vessels in the brain becomes sufficiently blocked so that oxygen deprivation in a region of the brain occurs. A frequent cause of stroke is that some or all of an atheroma becomes dislodged, and is carried by the natural blood flow to one of the vessels feeding the brain, where it creates a blockage resulting in the aforementioned oxygen deprivation.

It is known that different types of deposits or plaque in the blood vessels have different tendencies to become dislodged, and therefore certain types of deposits or plaque are more likely to create a risk of stroke than other types. It is known that plaque formed by calcifications and fibrous tissue, such as connective tissue and scar tissue, is less likely to become dislodged from the vessel wall than plaque formed by lipids. Currently, however, there is no imaging technique which allows these different types of plaques to be classified so that the risk or potential for dislodgement, and thus a stroke, can be assessed.

SUMMARY OF THE INVENTION

It is an object of the present invention to provide a method and apparatus for classifying plaque, thereby also allowing a risk diagnosis to be made as to the propensity of a patient to experience a stroke.

The above object is achieved in accordance with the principles of the present invention in a method and apparatus for classifying plaque in a blood vessel of a living subject using magnetic resonance imaging, wherein a first magnetic resonance image is produced with a first intensity distribution of a cross-section of a vessel containing plaque, and wherein a contrast agent is injected into the vascular system and a second magnetic resonance image of the cross-section of the vessel is produced with a second intensity distribution after a first time duration following the contrast agent injection, and wherein a third magnetic resonance image of the cross-section of the vessel is produced with a third intensity distribution after a second time duration following the injection of the contrast agent, and wherein the plaque is classified dependent on the respective intensity distributions of the magnetic resonance images.

The inventive method and apparatus allow classification of the plaque as being of a type known to be stable or prone to dislodgement. If the plaque is classified as being of the latter type, the patient is then at a higher risk of experiencing a stroke, due to dislodgement of the plaque and appropriate preventative steps can be taken. The preventative steps can range from dietary changes to pharmacological treatment to surgical intervention, dependent on the degree of risk which is diagnosed to exist.

As in any imaging employing the injection of a contrast agent, the tissue under examination will exhibit an enrichment phase during which the amount of contrast agent absorbed into the tissue in question will increase. This enrichment phase is then followed by a flushing phase, wherein the contrast agent is naturally eliminated from the tissue in question.

In an embodiment of the invention, the first time duration lies within the enrichment phase of the contrast agent in the plaque. In a further version of this embodiment, the second time duration lies within the flushing phase of the contrast agent in the plaque, following the enrichment phase. The first and second time durations can be in the range of minutes.

For insuring that the respective intensity distributions in the first, second and third magnetic resonance images are comparable to or correlated with each other, the same region in each of those images can be specified or defined, and the aforementioned intensity distributions within that region can be compared. Specifically, the intensity distributions in each image can be determined along a line through the cross-section of the vessel.

The classification of the plaque can include a first classification group including fat deposits (lipids). Another classification group can include small vessels (neo-vessels).

Such small vessels (neo-vessels) in the vessel wall will flush the contrast agent with a different time dynamic than lipids, wherein the contrast agent is located in the fatty cell interspaces and is flushed from those interspaces.

A third classification group can be inflammations, and a fourth classification group can include connective tissue and scar tissue (fibrous tissue). A further classification group can include calcifications.

Preferably the aforementioned magnetic resonance images are produced with a known FLASH sequence. Preferably the known contrast agent Gd-DTPA is employed as the contrast agent.

DESCRIPTION OF THE PREFERRED EMBODIMENTS

Figure 1:
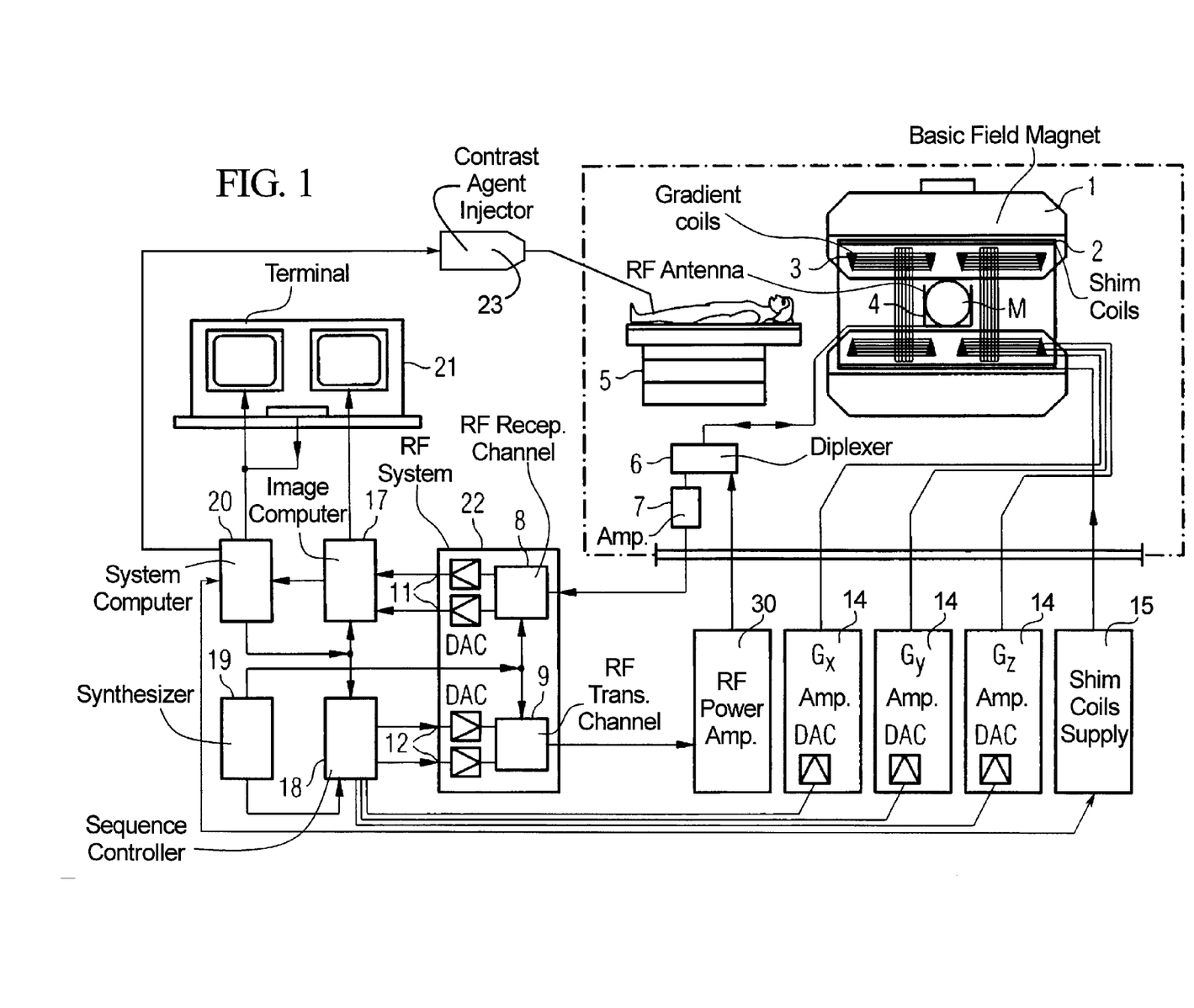
FIG. 1 is a schematic block diagram of a magnetic resonance imaging apparatus operable in accordance with the inventive method.

FIG. 1 is a schematic illustration of a magnetic resonance tomography apparatus for implementing the inventive method. The basic components of the magnetic resonance tomography apparatus correspond to those of a conventional tomography apparatus, with the differences discussed below. A basic field magnet 1 generates a temporally constant, strong magnetic field for the polarization or alignment of the nuclear spins in the examination region of a subject such as, for example, a part of a human body to be examined. The high homogeneity of the basic magnetic field required for the magnetic resonance measurement is defined in a spherical measurement volume M into which the parts of the human body to be examined are introduced. For satisfying the homogeneity requirements and, in particular, for eliminating time-invariable influences, shim plates of ferromagnetic material are attached at suitable locations. Time-variable influences are eliminated by shim coils 2 that are driven by a shim power supply 15.

A cylindrical gradient coil system 3 that is composed of three sub-windings is introduced into the basic field magnet 1. Each sub-winding is supplied with current by an amplifier 14 for generating a linear gradient field in one direction of the Cartesian coordinate system. The first sub-winding of the gradient field system generates a gradient $G_x$ in the x-direction, the second sub-winding generates a gradient $G_y$ in the y-direction and the third sub-winding generates a gradient $G_z$ in the x-direction. Each amplifier 14 has a digital-to-analog converter that is driven by a sequence controller 18 for the temporally correct generation of gradient pulses.

A radio-frequency antenna 4 is situated within the gradient field system 3. This antenna 4 converts the radio-frequency pulse output by a radio-frequency power amplifier 30 into a magnetic alternating field for exciting the nuclei and alignment of the nuclear spins of the examination subject or of the region of the subject to be examined. Usually a pulse sequence is employed having one or more radio frequency pulses and one or more gradient pulses The radio-frequency antenna 4 also converts the alternating field emanating from the precessing nuclear spins, i.e. the nuclear spin echo signals, into a voltage that is supplied via an amplifier 7 to a radio-frequency reception channel 8 of a radio-frequency system 22. The radio-frequency system 22 also has a transmission channel 9 in which the radio-frequency pulses for exciting the nuclear magnetic resonance are generated. The respective radio-frequency pulses are digitally represented as a sequence of complex numbers in the sequence controller 18 on the basis of a pulse sequence prescribed by the system computer 20. As a real part and an imaginary part, this number sequence is supplied via an input 12 to a digital-to-analog converter in the radio-frequency system 22 and from the latter to a transmission channel 9. In the transmission channel 9, the pulse sequences are modulated onto a high-frequency carrier signal having a base frequency corresponding to the resonant frequency of the nuclear spins in the measurement volume.

The switching from transmission mode to reception mode ensues via a transmission-reception diplexer 6. The radio-frequency antenna 4 emits the radio-frequency pulses for exciting the nuclear spins into the measurement volume M and samples resulting echo signals. The correspondingly acquired magnetic resonance signals are phase-sensitively demodulated in the reception channel 8 of the radio-frequency system 22 and converted via a respective analog-to-digital converters into a real part and an imaginary part of the measured signal. An image computer 17 reconstructs an image from the measured data acquired in this way. The management of the measured data, of the image data and of the control programs ensues via the system computer 20. On the basis of control programs, the sequence controller 18 controls the generation of the desired pulse sequences and the corresponding sampling of k-space. In particular, the sequence controller 18 controls the temporally correct switching of the gradients, the emission of the radio-frequency pulses with defined phase and amplitude as well as the reception of the magnetic resonance signals. The time base (clock) for the radio-frequency system 22 and the sequence controller 18 is made available by a synthesizer 19. The selection of suitable control programs for generating a magnetic resonance image as well as the presentation of the generated magnetic resonance image ensue via a terminal 21 that has a keyboard as well as one or more picture screens.

A contrast agent injector 23 is connected to a patient on the patient support 5, via a catheter, and is controlled by the system computer 20 as to the timing of the contrast agent injections. Manual control also is possible.

The system computer 20, together with the sequence controller 18, operates the magnetic resonance scanner, and the system computer 20 operates the contrast agent injector 23 in synchronism with each other so as to obtain a series of magnetic resonance images of the cross-section of a designated vessel that is known to contain plaque or is suspected of containing plaque. In the exemplary embodiment, images of a cross-section of the carotid artery are obtained.

Figure 2:
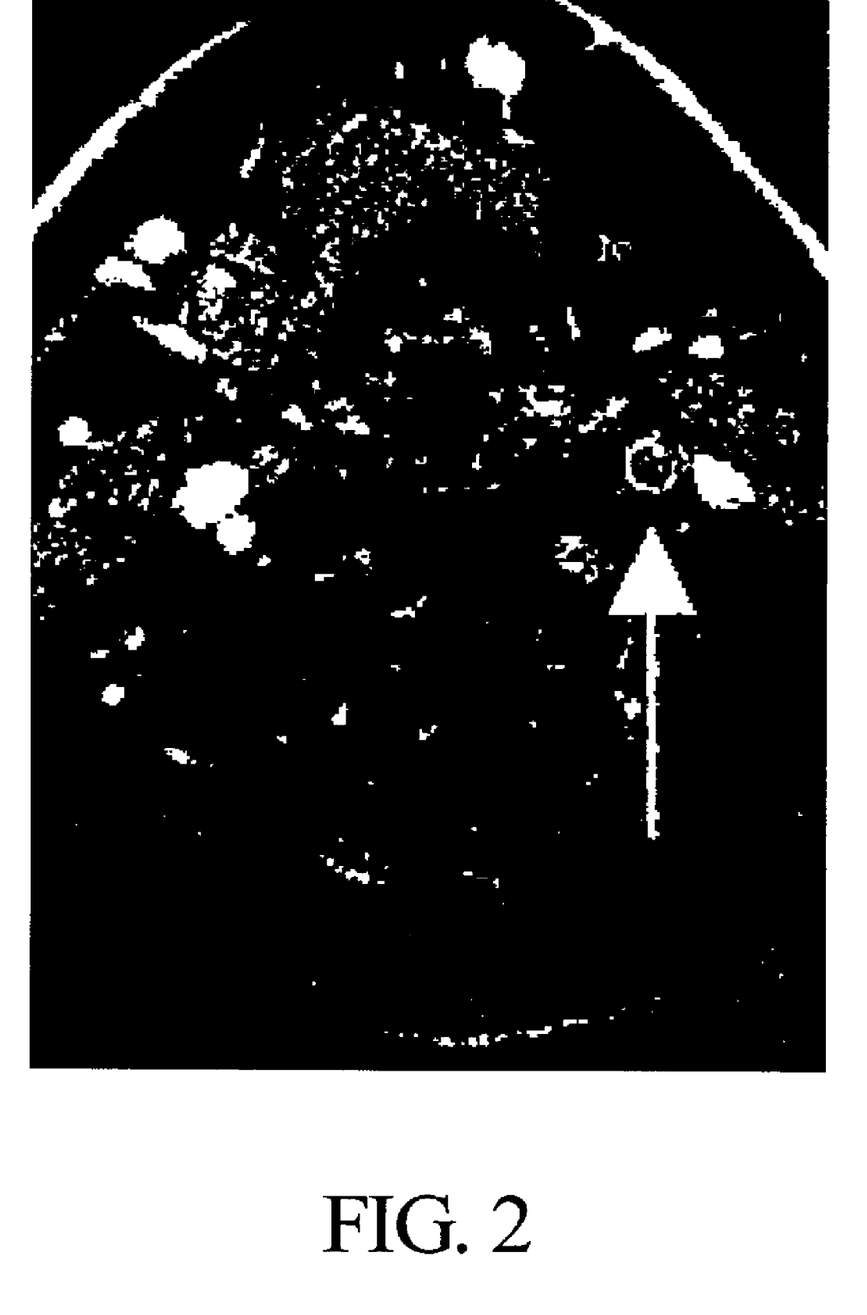
FIG. 2 is a magnetic resonance image of the type obtained in accordance with the inventive method showing contrast agent absorption in plaque in the carotid artery, in an overview image.

FIG. 2 is an overall image of a slice of the patient containing the carotid artery in cross-section.

Figure 3:
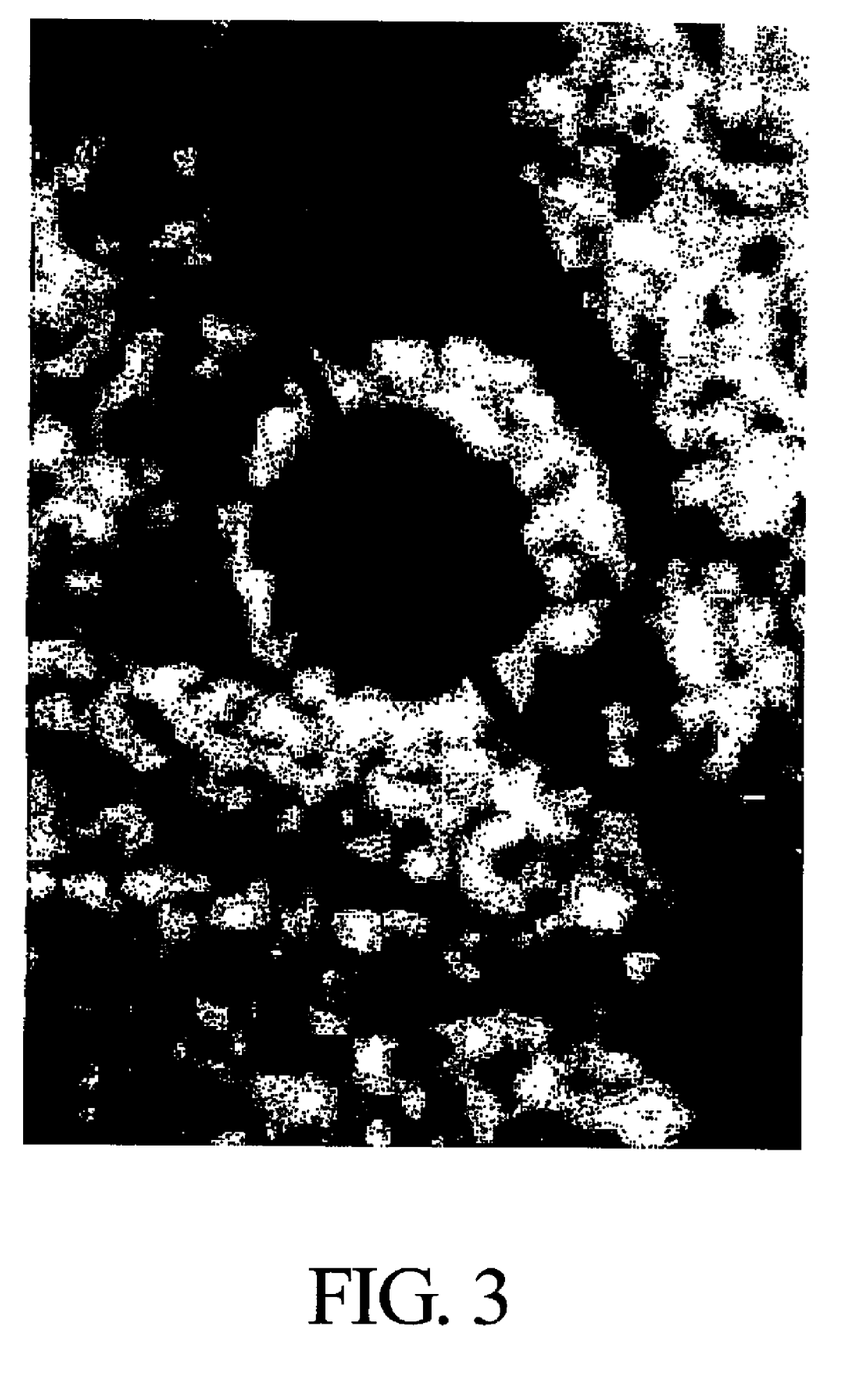
FIGS. 3, 4 and 5 are magnified exposures of the carotid artery shown in FIG. 2, showing contrast agent absorption in plaque in the carotid artery in accordance with the inventive method.
Figure 4:
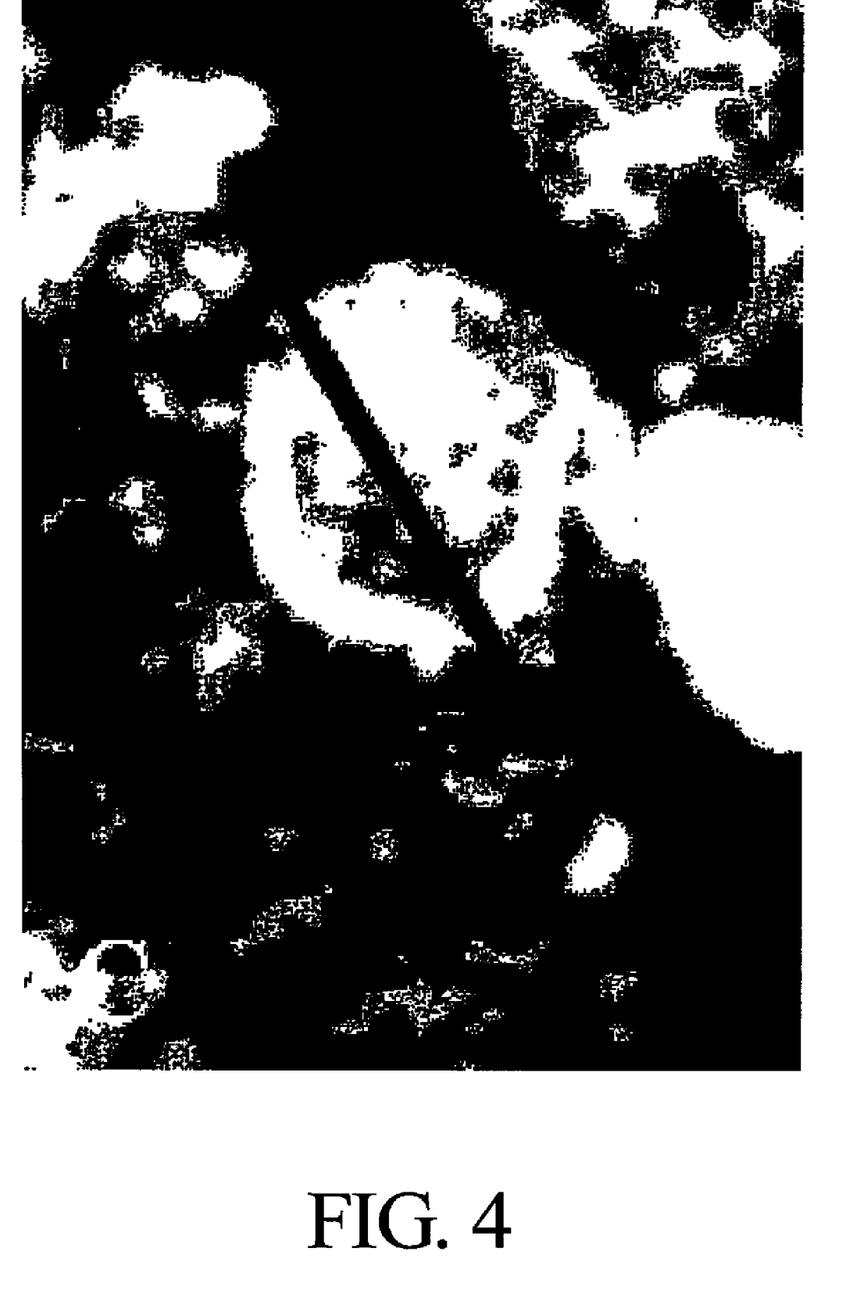

FIG. 3 is a first magnetic resonance image that is obtained with a first intensity distribution of the cross-section of the carotid artery that contains plaque, before the contrast agent injector 23 is operated to inject contrast agent. After obtaining the data for the image shown in FIG. 2, the system computer 20 operates the contrast agent injector 23 to inject contrast agent into the vascular system of the patient. After a first time duration, following the contrast agent injection, data for a second magnetic resonance image of the same vessel cross-section with a second intensity distribution are obtained. Such a second magnetic resonance image is shown in FIG. 4, wherein it can be seen that the plaque has absorbed the contrast agent.

Figure 5:
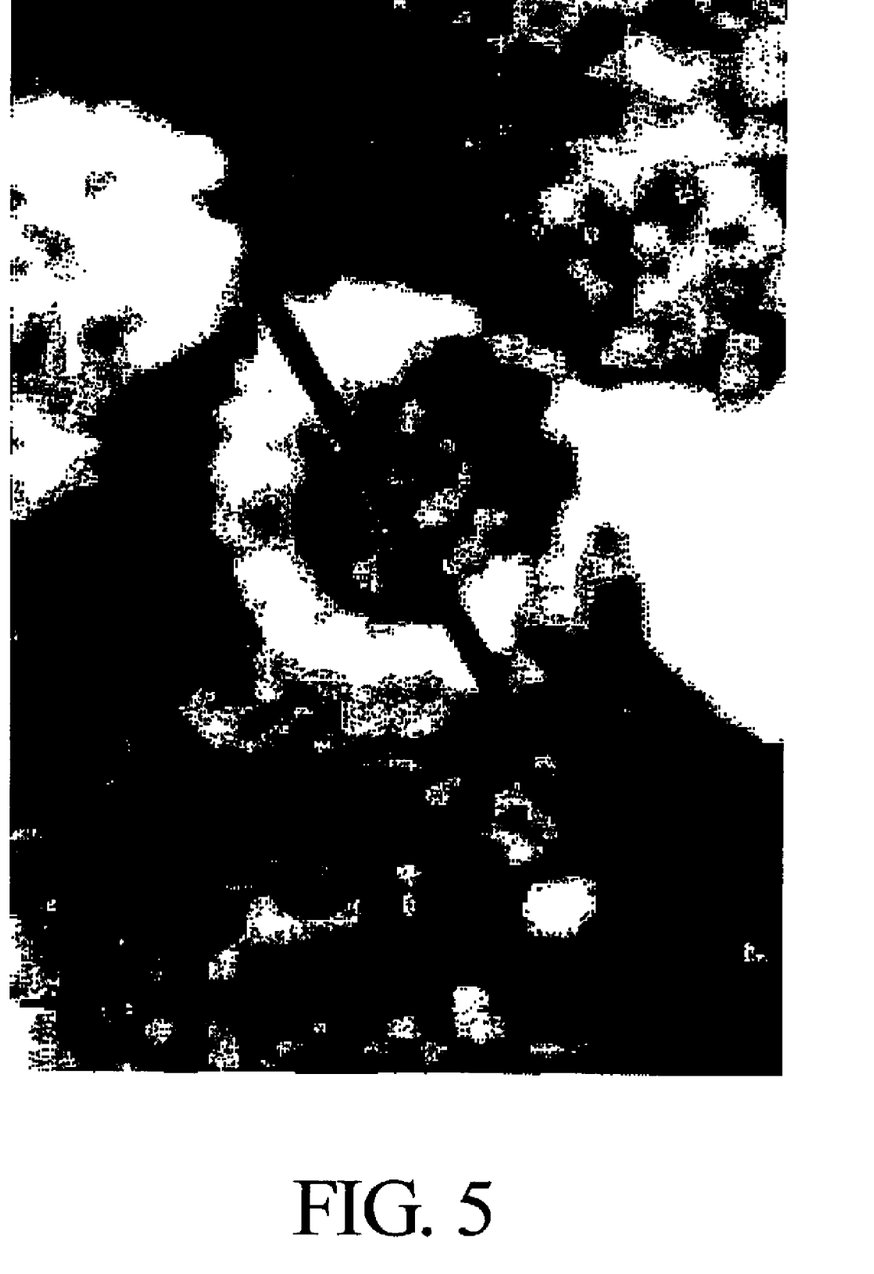

After a second time duration following the contrast agent injection, data for a third magnetic resonance image of the same vessel cross-section, with a third intensity distribution, are obtained. This third magnetic resonance image is shown in FIG. 5 wherein, in comparison to FIG. 4, it can be seen that contrast agent has begun to be flushed out of the plaque.

Figure 6:
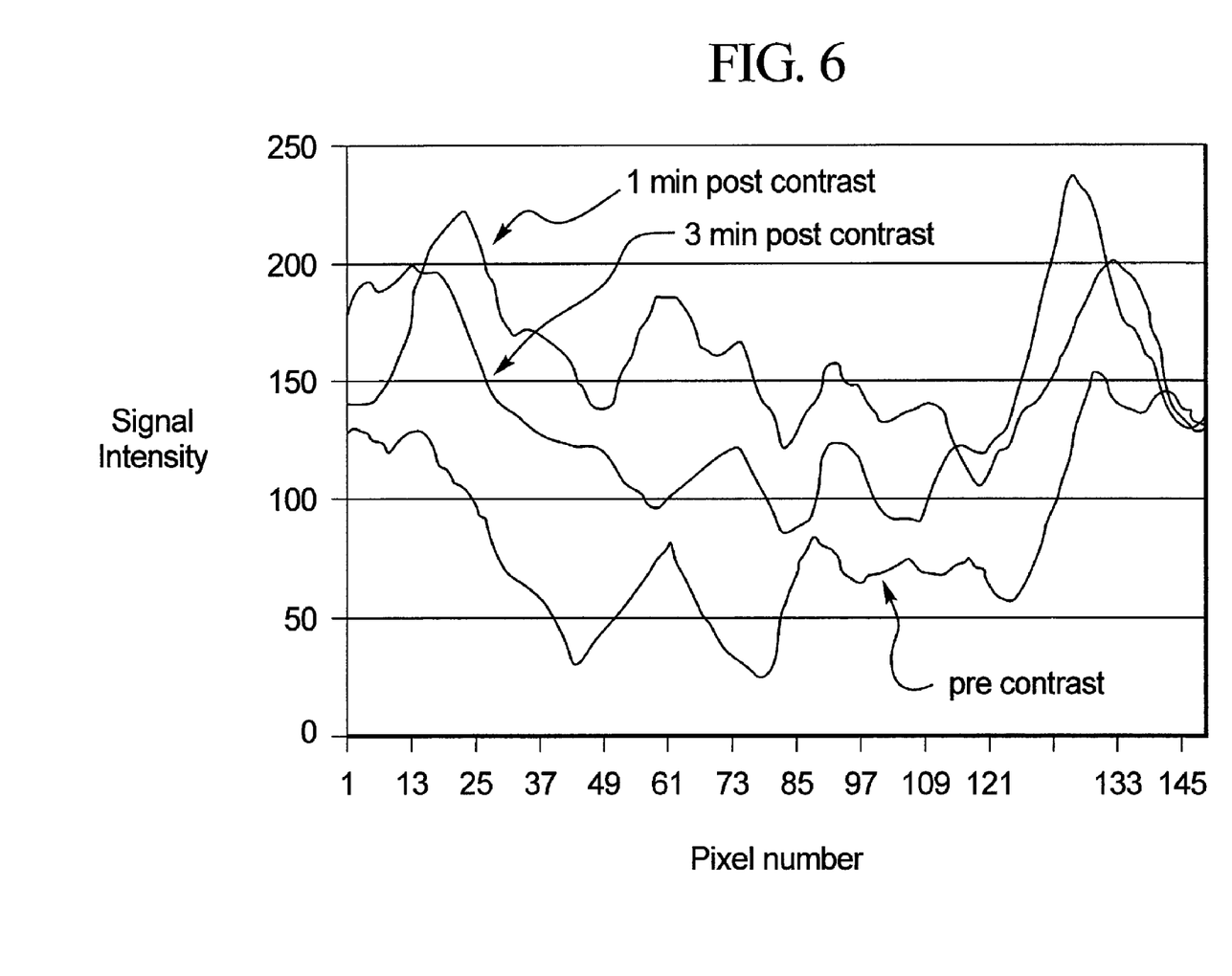
FIG. 6 is a profile curve illustrating the intensity distribution in accordance with the inventive method.

Curves of the signal intensity distribution are shown in FIG. 6, for an image before the contrast agent is injected, and, as examples, curves respectively showing the signal intensity one minute after the injection of the contrast agent and three minutes after the injection of the contrast agent.

Based on these signal intensity distributions, and preferably employing a suitably programmed automatic electronic classifier, the plaque is classified. The terminal 21 can execute a classifier program, for example, or the data can be transferred to some other computer and/or to some other location for undertaking the classifications.

Preferably the first time duration, after which the second magnetic resonance image shown in FIG. 3 is obtained, is within the enrichment phase of the contrast agent in the plaque, and preferably the second time duration, after which the third magnetic resonance image shown in FIG. 4 is obtained, is within the flushing phase of the contrast agent in the plaque. As indicated in FIGS. 3, 4 and 5, the intensity distribution can be measured along a defined line in the images.

The classification of the plaque can include a number of classes, such as a class for plaque composed of deposits (lipids), a class for plaque composed of small vessels (neo-vessels), a class for plaque formed by inflammations, a class for plaque formed by fibrous tissue (connective tissue or scar tissue), and a class for plaque composed of calcifications.

Preferably, the system computer 20 and the sequence controller 18 operate the magnetic resonance scanner in a known FLASH sequence for obtaining the images shown in FIGS. 2, 3, 4 and 5.

The contrast agent employed preferably is Gd-DTPA, which is a known contrast agent for magnetic resonance imaging.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computerized method for classifying plaque in a blood vessel of a living subject comprising the steps of:
   implementing a magnetic resonance imaging sequence to obtain data representing a first magnetic resonance image with a first intensity distribution of a cross-section of a vessel containing plaque in a living subject;
   injecting contrast agent that interacts with said plaque into the vascular system of said subject, said contrast agent interacting non-uniformly with said plaque with respect to time and thus producing different intensity distributions in said plaque in a time period;
   in said time period, re-implementing said magnetic resonance imaging sequence to obtain data representing a second magnetic resonance image of said cross-section of said vessel and said plaque therein with a second intensity distribution after a first time duration following injection of said contrast agent;
   in said time period, again re-implementing said magnetic resonance imaging sequence to obtain data representing a third magnetic resonance image of said cross-section of said vessel and said plaque therein with a third intensity distribution after a second time duration following injection of said contrast agent, said second and third intensity distributions differing from each other due to said non-uniform interaction of said contrast agent with said plaque in said time period; and
   in a computer, classifying said plaque dependent on said first, second and third intensity distributions to produce a classification result and presenting said classification result in a visually perceptible display at said computer.

2. A method as claimed in claim 1 comprising classifying said plaque in different classes of plaque dependent on propensity to dislodge from said vessel.

3. A method as claimed in claim 1 comprising selecting said first time duration to lie within an enrichment phase of said contrast agent in said plaque.

4. A method as claimed in claim 1 comprising selecting said time duration as approximately one minute.

5. A method as claimed in claim 3 comprising selecting said second time duration to lie within a flushing phase of said contrast agent in said plaque, following said enrichment phase.

6. A method as claimed in claim 5 comprising selecting said second time duration as approximately three minutes.

7. A method as claimed in claim 1 comprising selecting a same region of said subject in each of said first, second and third magnetic resonance images and determining the respective first, second and third intensity distributions in said region.

8. A method as claimed in claim 7 comprising defining a same line in each of said first, second and third magnetic resonance images, and determining the respective first, second and third intensity distributions along said line.

9. A method as claimed in claim 1 comprising classifying said plaque in a plurality of classes including a class representing plaque composed of fat deposits.

10. A method as claimed in claim 1 comprising classifying said plaque in a plurality of classes including a class representing plaque composed of small vessels.

11. A method as claimed in claim 1 comprising classifying said plaque in a plurality of classes including a class representing plaque composed of inflammations.

12. A method as claimed in claim 1 comprising classifying said plaque in a plurality of classes including a class representing plaque composed of fibrous tissue.

13. A method as claimed in claim 1 comprising classifying said plaque in a plurality of classes including a class representing plaque composed of calcifications.

14. A method as claimed in claim 1 wherein the step of classifying said plaque comprises classifying said plaque in respective classes representing plaque composed of deposits, plaque composed of small vessels, plaque composed of inflammations, plaque composed of fibrous tissue, and plaque composed of calcifications.

15. A method as claimed in claim 1 comprising obtaining said data for said first, second and third magnetic resonance images using a FLASH sequence.

16. A method as claimed in claim 1 comprising injecting Gd-DTPA into the vascular system of said subject as said contrast agent.

17. A magnetic resonance imaging apparatus comprising:
   a magnetic resonance scanner adapted to receive a living subject therein, said subject having a vascular system with vessels containing plaque;
   a contrast agent injector adapted to inject contrast agent, that interacts with said plaque, into the vascular system of the living subject situated in said magnetic resonance scanner, said contrast agent interacting non-uniformly with said plaque with respect to time and thus producing different intensity distributions in said plaque in a time period;
   a system computer connected to said magnetic resonance scanner for operating said magnetic resonance scanner to implement a magnetic resonance imaging sequence to obtain data representing a first magnetic resonance image with a first intensity distribution of a cross-section of a vessel at the subject and said plaque therein, of said subject before injecting said contrast agent, and to re-implement said magnetic resonance imaging sequence to obtain data in said time period that represent a second magnetic resonance image of said cross-section of said vessel and said plaque therein with a second intensity distribution after a first time duration following injection of said contrast agent, and to again re-implement said magnetic resonance imaging sequence to obtain data in said time period that represent a third magnetic resonance image of said cross-section of said vessel and said plaque therein with a third intensity distribution after a second time duration following injection of said contrast agent, said second and third intensity distributions differing from each other due to said non-uniform interaction of said contrast agent with said plaque in said time period; and
   a diagnostic computer supplied with said data for said first, second and third magnetic resonance images for classifying said plaque dependent on said first, second and third intensity distributions.

18. An apparatus as claimed in claim 17 wherein said diagnostic computer classifies said plaque in different classes of plaque dependent on propensity to dislodge from said vessel.

19. An apparatus as claimed in claim 17 wherein said system computer sets said first time duration to lie within an enrichment phase of said contrast agent in said plaque.

20. An apparatus as claimed in claim 17 wherein said system computer sets said time duration as approximately one minute.

21. An apparatus as claimed in claim 19 wherein said system computer sets said second time duration to lie within a flushing phase of said contrast agent in said plaque, following said enrichment phase.

22. An apparatus as claimed in claim 21 wherein said system computer sets said second time duration as approximately three minutes.

23. An apparatus as claimed in claim 17 wherein said system computer operates said magnetic resonance scanner to obtain data from a same region of said subject in each of said first, second and third magnetic resonance images and wherein said diagnostic computer determines the respective first, second and third intensity distributions in said region.

24. An apparatus as claimed in claim 23 wherein said diagnostic computer defines a same line in each of said first, second and third magnetic resonance images, and determines the respective first, second and third intensity distributions along said line.

25. An apparatus as claimed in claim 17 wherein said diagnostic computer classifies said plaque in a plurality of classes including a class representing plaque composed of fat deposits.

26. An apparatus as claimed in claim 17 wherein said diagnostic computer classifies said plaque in a plurality of classes including a class representing plaque composed of small vessels.

27. An apparatus as claimed in claim 17 wherein said diagnostic computer classifies said plaque in a plurality of classes including a class representing plaque composed of inflammations.

28. An apparatus as claimed in claim 17 wherein said diagnostic computer classifies said plaque in a plurality of classes including a class representing plaque composed of fibrous tissue.

29. An apparatus as claimed in claim 17 wherein said diagnostic computer classifies said plaque in a plurality of classes including a class representing plaque composed of calcifications.

30. An apparatus as claimed in claim 17 wherein said diagnostic computer classifies said plaque in respective classes representing plaque composed of deposits, plaque composed of small vessels, plaque composed of inflammations, plaque composed of fibrous tissue, and plaque composed of calcifications.

31. An apparatus as claimed in claim 17 wherein said system computer operates said magnetic resonance scanner to obtain said data for said first, second and third magnetic resonance images using a FLASH sequence.

32. An apparatus as claimed in claim 17 wherein said contrast agent injector injects Gd-DTPA into the vascular system of said subject as said contrast agent.

33. An apparatus as claimed in claim 17 wherein said contrast agent injector is operated by said system computer to inject said contrast agent.

* * * * *